(12) United States Patent
Graham et al.

(10) Patent No.: US 7,919,458 B2
(45) Date of Patent: Apr. 5, 2011

(54) METHOD OF INHIBITING PROSTATE CANCER CELL PROLIFERATION

(75) Inventors: Garry George Graham, Kensington (AU); Qihan Dong, Abbortsford (AU)

(73) Assignee: Scott, Kieran, Francis, New South Wales (AU)

( * ) Notice: Subject to any disclaimer, the term of this patent is extended or adjusted under 35 U.S.C. 154(b) by 1052 days.

(21) Appl. No.: 10/517,256

(22) PCT Filed: Jun. 10, 2003

(86) PCT No.: PCT/AU03/00719
§ 371 (c)(1),
(2), (4) Date: Jan. 14, 2005

(87) PCT Pub. No.: WO2004/064822
PCT Pub. Date: Aug. 5, 2004

(65) Prior Publication Data
US 2008/0113343 A1 May 15, 2008

(30) Foreign Application Priority Data
Jun. 7, 2002 (AU) ........................... PS2826

(51) Int. Cl.
*A61K 38/12* (2006.01)
(52) U.S. Cl. ............ 514/9; 530/300; 530/317; 530/330; 530/350; 514/2; 514/17
(58) Field of Classification Search ................. 514/2, 9, 514/11, 17; 530/300, 317, 330, 333, 350
See application file for complete search history.

(56) References Cited

U.S. PATENT DOCUMENTS
5,656,602 A 8/1997 Tseng et al.
5,942,402 A 8/1999 Schmidt et al.

FOREIGN PATENT DOCUMENTS
| EP | 1 300 159 A1 | 4/2003 |
| EP | 1 329 511 A1 | 7/2003 |
| WO | WO 96/40657 A1 | 12/1996 |
| WO | WO 98/05349 A | 2/1998 |
| WO | WO 98/05349 A1 | 2/1998 |
| WO | WO 02/24923 A1 | 3/2002 |
| WO | WO 02/38575 A1 | 5/2002 |
| WO | WO 03/014082 A1 | 2/2003 |

OTHER PUBLICATIONS

Markova et al. (Oncogene. Sep. 22, 2005; 24 (42): 6450-6458).*
Murkami et al. (J. Biochem. Mar. 2002; 131 (3): 285-292).*
Masuda et al. (Biochim. Biophys. Acta. 2005; 1736: 200-210).*
Suzuki et al. (J. Biol. Chem. Feb. 25, 2000; 275 (8): 5785-5793).*
Menschikowski et al. (Neoplasia. Mar. 2008; 10 (3): 279-286).*
Finjeman et al. (Front. Biosci. May 1, 2008; 13: 4144-4174).*
Rose et al. (Prostate. 1991; 18 (3): 243-254).*
Jaulmes et al. (Arterioscler. Thromb. Vasc. Biol. Jun. 2005; 25 (6): 1161-1167).*
Kelland et al. (Eur. J. Cancer. Apr. 2004; 40 (6): 827-836).*
Tseng et al. (J. Biol. Chem. Sep. 27, 1996; 271 (39): 23992-23998).*
Gura (Science. 1997; 278: 1041-1042).*
Dennis (Nature. Aug. 7, 2006; 442: 739-741).*
Schuh (Toxicologic Pathology. 2004; 32 (Suppl. 1): 53-66).*
Bibby (Eur. J. Cancer. Apr. 2004; 40 (6): 852-857).*
Peterson et al. (Eur. J. Cancer. 2004; 40: 837-844).*
Saijo et al. (Cancer Sci. Oct. 2004; 95 (10): 772-776).*
Sved et al. (Cancer Res. Oct. 1, 2004; 64: 6934-6940).*
Thwin et al. (J. Med. Chem. 2007; 50: 5938-5950).*
Church et al. (J. Biol. Chem. Aug. 31, 2001; 276 (35): 33156-33164).*
Liu et al. (J. Urol. Sep. 2000; 164: 820-825).*
Kelavkar et al. (Carcinogenesis. Nov. 2001; 22 (11): 1765-1773).*
Patel et al. (Clin. Cancer Res. Dec. 15, 2008; 14 (24): 8070-8079).*
Dong et al. (Cancer Lett. Aug. 18, 2006; 240 (1): 9-16).*
Scott et al. (Biochimie. Jun. 2010; 92 (6): 601-610).*
Attiga, F.A., et al; "Inhibitors of Prostaglandin Synthesis Inhibit Human Prostate Tumour Cell Invasiveness and Reduce the Release of Matrix Metalloproteinases"; *Cancer Research*, vol. 60, pp. 4629-4637 (2000).
De Souza, P.L., et al; "Enhancement of Paclitaxel Activity Against Hormone-Refractory Prostate Cancer Cells in Vitro and in Vivo by Quinacrine"; *British Journal of Cancer*; vol. 75(11); pp. 1593-1600 (1997).
Jiang, J., et al; "Expression of Group IIA Secretory Phospholipase A2 Is Elevated in Prostatic Intraepithelial Neoplasia and Adenocarcinoma"; *American Journal of Pathology*; vol. 160, No. 2; pp. 667-670; (2002).
Graff, J.R., et al; "Expression of Group IIA Secretory Phospholipase A2 Increases with Prostate Tumor Grade"; *Clinical Cancer Research*; vol. 7; pp. 3857-3861 (2001).
Lehr, M.; "Phospholipase $A_2$ Inhibitors in Inflammation"; *Expert Opinion*; Ashley Publications; pp. 1123-1136 (2001).
Scott, K.F., et al; "Secreted Phospholipase $A_2$ Enzymes as Therapeutic Targets"; *Expert Opinion*; Ashley Publications; pp. 1-14 (2003).
Ono, T., et al; "Characterization of a novel inhibitor of cytosolic phospholipase $A_2\alpha$, pyrrophenone"; *Biochem, J.*; vol. 363; pp. 727-735 (2002) (XP-002532197).
Sved, P., et al; "Oncogenic Action of Secreted Phospholipase $A_2$ in Prostate Cancer"; *Cancer Research*; vol. 64; pp. 6934-6940 (2004) (XP-002532198).

* cited by examiner

*Primary Examiner* — Stephen L Rawlings
(74) *Attorney, Agent, or Firm* — Nixon & Vanderhye

(57) ABSTRACT

The present invention relates to a method of inhibiting or reducing the proliferation of prostate cancer cells, such as androgen independent prostate cancer (AIPC) cells, the method comprising administering to the cells a $PLA_2$ inhibitor. In one embodiment the $PLA_2$ inhibitor is a conformationally constrained molecule derived from a peptide consisting essentially of amino acid residues 70-74 of a human $sPLA_2$-IIA protein, or the equivalent residues in other $sPLA_2$ proteins.

3 Claims, 4 Drawing Sheets

METHOD OF INHIBITING PROSTATE CANCER CELL PROLIFERATION

This application is the U.S. National Phase of International Application PCT/AU2003/00719, filed 10 Jun. 2003, which designated the U.S. PCT/AU2003/00719 claims priority to Australian Application No. PS 2826 filed 7 Jun. 2002. The entire content of these applications are incorporated herein by reference.

FIELD OF THE INVENTION

The present invention relates to a method of inhibiting proliferation of prostate cancer cells, such as in a method of treating prostate cancer. In particular, the invention relates to a method of inhibiting proliferation of androgen-independent prostate cancer cells.

BACKGROUND OF THE INVENTION

Prostate cancer occurs frequently in men, is currently the second most common cause of cancer-related death and incidence is growing. Prostatectomy is useful in the treatment of patients with cancer confined to the prostate. Androgen ablation therapy is used in cases where cancer cells still require androgens for growth but have spread beyond the prostate. To date, however, there is no effective treatment for metastatic Androgen-independent Prostate Cancer (AIPC).

Our understanding of the aetiology of prostate cancer is limited and unlike certain other cancers, little progress has been made in elucidating its cause. Efforts have been made to identify genes responsible for familial prostate cancer. At least seven chromosomal loci have been reported, however the genes responsible for prostate cancer in all these loci have not yet been identified. Although an inherited genetic predisposition occurs in only 5-10% of cases, it is possible that identification of germline mutations may shed light on sporadic cases as both forms share the same histopathological features. The majority of researchers have focused on somatic defects in sporadic prostate cancer. Classical cytogenetic studies are difficult to apply to solid tumours and so far no consistent chromosomal changes have been observed. Although comparative genome hybridisation and loss of heterozygosity analysis have shown both gain and loss of genomic DNA, the majority of genes involved are still unknown. Oncogenes and tumour suppressor genes known to be associated with other malignancies have a remarkably low frequency of mutation or deletion in prostate cancer. Using technologies that compare the steady-state mRNA levels between normal and cancerous prostate, a list of genes have been revealed to be either over or underexpressed in prostate cancer tissue or cell-lines. Although proteomics and tissue array approaches are now being used, relatively few genes have yet been verified to be differentially expressed in a reasonable number of specimens at the protein level. Direct evidence for the importance of these differentially expressed genes in prostate cancer initiation or progression is lacking. As a result, although progress is rapid, the application of this new knowledge in controlling mortality and morbidity from prostate cancer is slow at present.

Emerging evidence from epidemiological studies indicates a strong association between prostate cancer risk and total fat intake (Kolonel et al., 1999 J. Natl Cancer Inst. 91: 414), although the biochemical link between dietary lipids and genesis of prostate cancer remains unclear. Previous studies have demonstrated that both cyclooxygenase (COX) and lipoxygenase (LOX) products of arachidonic acid metabolism, the prostaglandins (PG), and hydroxyeicosatetraenoic acids (HETES) respectively, contribute to formation and/or progression of prostate cancer. They are implicated in promotion of tumour cell proliferation, motility, invasion and metastasis, and induction of angiogenesis both in vitro and in animal models. Interestingly, arachidonic acid levels are lower in malignant than benign (BPH) prostate tissue while PG and HETE synthesis from labelled arachidonic acid is significantly increased. However, the activity of arachidonic acid mobilising enzymes phospholipase $A_2$ ($PLA_2$) and fatty acyl-CoA lysophosphatidylcholine acyltransferase, are also increased, suggesting an increased flux of arachidonic acid through the COX and LOX pathways.

$PLA_2$ constitutes a large and diverse family of enzymes that catalyse the hydrolysis of membrane phospholipids at the sn-2 position to release fatty acids and lysophospholipids. $PLA_2$ enzymes are classified according to their source and their cellular location (i.e secreted $PLA_2$ enzymes ($sPLA_2s$) or cytosolic $PLA_2$ enzymes ($cPLA_2s$)). A review of the classification and characterisation of the expanding superfamily of $PLA_2$ enzymes had been published by Six and Dennis (2000) *Biochim. Biophys. Acta* 1488:1-19.

$sPLA_2$-IIA is elevated in prostate cancer (Graff et al., 2001, Clin. Cancer Res. 7: 3857-3861; Jiang et al., 2002, Am. J. Pathol. 160: 667-671) and enhanced $sPLA_2$-IIA expression has been inversely related to 5-year patient survival (Graff et al., 2001). In addition, the chromosomal location of several $sPLA_2$ genes including $sPLA_2$-IIA (1p35-ter), overlaps with one prostate cancer susceptibility locus CAPB (Nwosu et al., 2001, Human Mol. Genet. 10: 2313-2318). To date, however, there has been no evidence to show that $sPLA_2$-IIA is involved in prostate tumorigenesis.

SUMMARY OF THE INVENTION

We have now shown by immunohistochemistry in patients following androgen ablation therapy, that Type IIA secreted phospholipase $A_2$ ($sPLA_2$-IIA) is elevated in androgen-independent tumour cells relative to benign glands, while cytosolic phospholipase $A_2$-α ($cPLA_2$-α) levels are unchanged.

We have also found that treatment of prostate cancer cells with $sPLA_2$-IIA potently increases proliferation of the cells, and that this proliferative effect is blocked by the addition of selective inhibitors of both $sPLA_2$-IIA and $cPLA_2$-α enzymes.

This provides evidence for the first time of the direct role of $PLA_2$ in the proliferation of prostate cancer cells and identifies this class of enzymes as an important therapeutic target for the treatment of prostate cancer.

Accordingly, in a first aspect the present invention provides a method of inhibiting or reducing the proliferation of prostate cancer cells, the method comprising administering to the cells a $PLA_2$ inhibitor.

In a second aspect the present invention provides a method for the treatment of prostate cancer, the method comprising administering to a subject in need thereof a $PLA_2$ inhibitor.

In a preferred embodiment of the first and second aspects, the prostate cancer cells are androgen independent prostate cancer (AIPC) cells.

In accordance with the first and second aspects of the present invention, the $PLA_2$ inhibitor may inhibit any $PLA_2$ enzyme. Preferably, the inhibitor inhibits an enzyme selected from group 1B, IIA, IID, IIE, IIF, III, IV, V, and X $PLA_2$ enzymes.

In one embodiment, the inhibitor is a $cPLA_2$-α inhibitor. For example, the inhibitor may be pyrrolidine-1, a substituted pyrimidine as described in WO 00/27824, a 9,10-dihydro-9, 10-ethanoanthracene derivative as described in WO 99/15493, an azalomycin inhibitor as described in JP12119292, an arylsulfonamide as described in WO 98/25893, an indole-2-carboxylic acid derivative as described in WO 98/05637, an indole derivative as described in WO 98/08818, WO 99/43651, WO 99/43654 or WO 99/43672, a 3-sulfanyl-propane-1,2-diol derivative as described in JP12038380, a heterocyclic compound such as those described in WO 00/34254 or an oxazolidinedione or thiazolidinedione derivative as described in WO 97/05135 or WO 98/33797.

In another embodiment, the inhibitor is an sPLA$_2$-IIA inhibitor. For example, the inhibitor may be a benzoic acid as described in JP8325154, a 6-aza-spiro-[4,5]-decane derivative as described in JP9110835, amide derivatives of fatty acids such as those described in WO 00/00220 and WO 95/19959, (arylsulfonamidophnoxy) benzoic acids such as those described in WO 97/35567, fatty acid derivatives such as those described in WO 97/38966, tetronic acids such as those described in JP0045740, dinitrogen heterocyclic compounds such as those described in WO 98/05332, oxadiazine and thioxadiazine derivatives such as those described in WO 00/71118, sulfonylaminopyrazoles such as those described in WO 98/24437, (Indol-3-yl)acetamide inhibitors described in EP 839806, EP 950657, EP 952149 and WO 00/07590, (indol-3-yl) oxoacetamides such as those described in EP 675110, WO 98/37069, WO 99/59999, WO 99/51605, WO 00/07591, WO 00/37358 and WO 00/00201, or derivatives such as those described in WO 99/21545, WO 99/21546 and WO 99/21559.

In a particularly preferred embodiment the inhibitor is a conformationally constrained molecule derived from a peptide consisting essentially of amino acid residues 70 to 74 of a human sPLA$_2$-IIA protein, or the equivalent residues in other sPLA$_2$-IIA proteins.

Preferably, the conformationally constrained molecule is a peptide, more preferably a cyclic peptide.

In a preferred embodiment, the conformationally constrained peptide is a cyclic peptide of the following formula:

A1-A2-A3-A4-A5 in which

A1 is F or Y or W or 2Nap
A2 is L or I
A3 is S or T
A4 is F or Y or W or 2Nap
A5 is R or K

In a further preferred embodiment of the present invention, the peptide is selected from the group consisting of cFLSYK (SEQ ID NO: 5), cFLSYR (SEQ ID NO: 6) and c (2NapA) LS (2NapA) R.

When used herein the term "cFLSYK" (SEQ ID NO: 5) means "cyclic FLSYK" (SEQ ID NO: 5), "cFLSYR" (SEQ ID NO: 6) means "cyclic FLSYR" (SEQ ID NO: 6) and "c(2NapA)LS(2NapA)R" means "cyclic (2Nap)LS (2Nap) R". The term "2NapA" is an abbreviation for 2-naphthylalanine.

In a further preferred embodiment, the peptide comprises D-amino acids and has a sequence which corresponds to the reverse sequence of a peptide according to the first aspect of the present invention.

In a preferred embodiment of the present invention, the method involves administration of a sPLA$_2$-IIA inhibitor in conjunction with a cPLA$_2$-α inhibitor.

In yet a further aspect the present invention provides the use of a PLA$_2$ inhibitor in the manufacture of a medicament for the treatment of prostate cancer.

In yet a further aspect the present invention provides the use of a conformationally constrained molecule derived from a peptide consisting essentially of amino acid residues 70 to 74 of a human sPLA$_2$-IIA protein, or the equivalent residues in other sPLA$_2$-IIA proteins, in the manufacture of a medicament for the treatment of prostate cancer.

In yet another aspect the present invention provides a method for detecting prostate cancer or a metastasis thereof in a subject, said method comprising:
determining the level of PLA$_2$ mRNA expressed in a test sample from said subject; and
comparing the level of PLA$_2$ mRNA determined at (i) to the level of PLA$_2$.mRNA expressed in a comparable sample from a healthy or normal individual,
wherein a level of PLA$_2$ mRNA at (i) that is enhanced in the test sample relative to the comparable sample from the normal or healthy individual is indicative of the presence of a cancer cell in said subject.

In yet another aspect the present invention provides a method for detecting prostate cancer or a metastases thereof in a subject, said method comprising:
determining the level of a PLA$_2$ polypeptide in a test sample from said subject; and
comparing the level of PLA$_2$ polypeptide determined at (i) to the level of said PLA$_2$ polypeptide in a comparable sample from a healthy or normal individual,
wherein a level of said PLA$_2$ polypeptide at (i) that is enhanced in the test sample relative to the comparable sample from the normal or healthy individual is indicative of the presence of a cancer cell in said subject.

In yet another aspect the present invention provides a method of assessing the predisposition of a subject to prostate cancer, the method comprising the step of determining the presence of a polymorphism or an epigenetic change in a PLA$_2$ gene of the subject.

$OD_{495}$ of unstimulated cells was 0.29±0.06 for sPLA$_2$-IIA and 0.24±0.03 for the sPLA$_2$-IIA mutant experiments in panel A and 0.24±0.03 for panel B. *p<0.05 vs untreated control by one-way ANOVA. Data are representative of three separate experiments. (C). LNCaP cells were grown as above and stimulated for 72 hours with sPLA$_2$-IIA (1 nM) in the absence (dotted lines) and presence (solid lines) of the sPLA$_2$-IIA inhibitor cFLSYR (SEQ ID NO: 6) (100 nM). Cells (1×10$^6$) were assayed by flow cytometry following treatment with propidium iodide as described in Materials and Methods. Statistical analysis was performed on 10,000 events per sample. Data are representative of three separate experiments.

Figure 3:
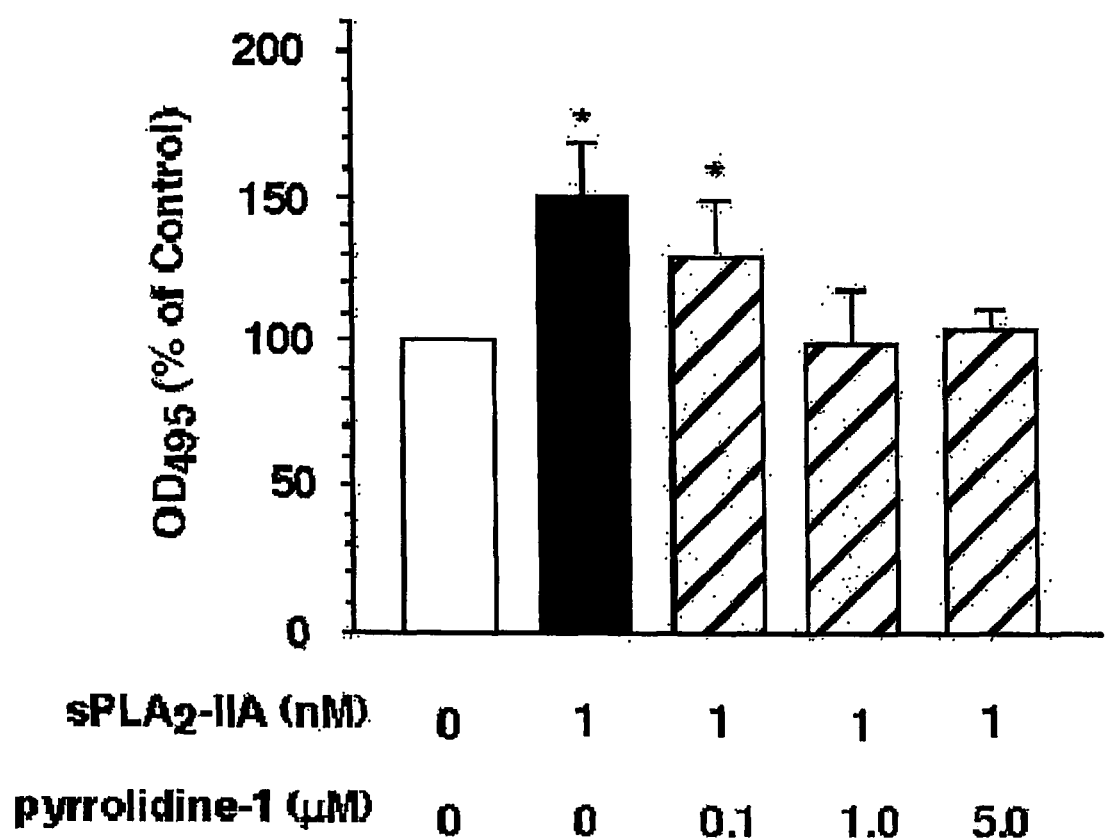

FIG. 3. Effect of inhibition of cPLA$_2$-α on sPLA$_2$-IIA-dependent proliferation. LNCaP cells were grown in RPMI containing 5% FCS and stimulated for 72 hours with sPLA$_2$-IIA (1 nM) in the presence (hatched bars) and absence (closed bar) of increasing concentrations of the cPLA$_2$-α-selective inhibitor pyrrolidine-1. Cell number was determined by the MTS assay as described in Materials and Methods. Data are mean±SD of quadruplicate determinations expressed as percentages relative to untreated control cells (100%) (open bar). $OD_{495}$ of untreated cells was 0.33±0.03. In the presence of pyrrolidine-1 (5 uM) alone, $OD_{495}$ was 0.38±0.04*p<0.05 vs untreated control by one-way ANOVA.

Figure 4:
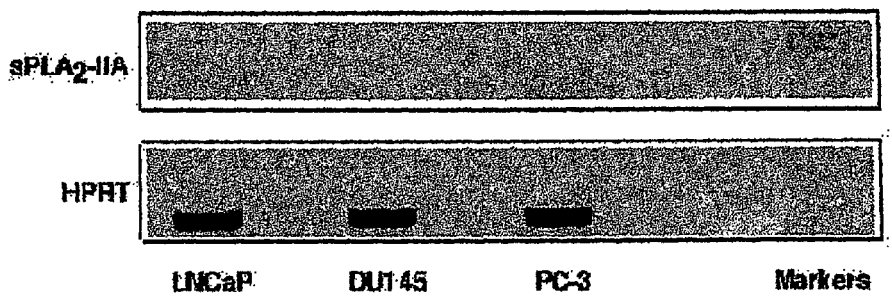
Figure 4:
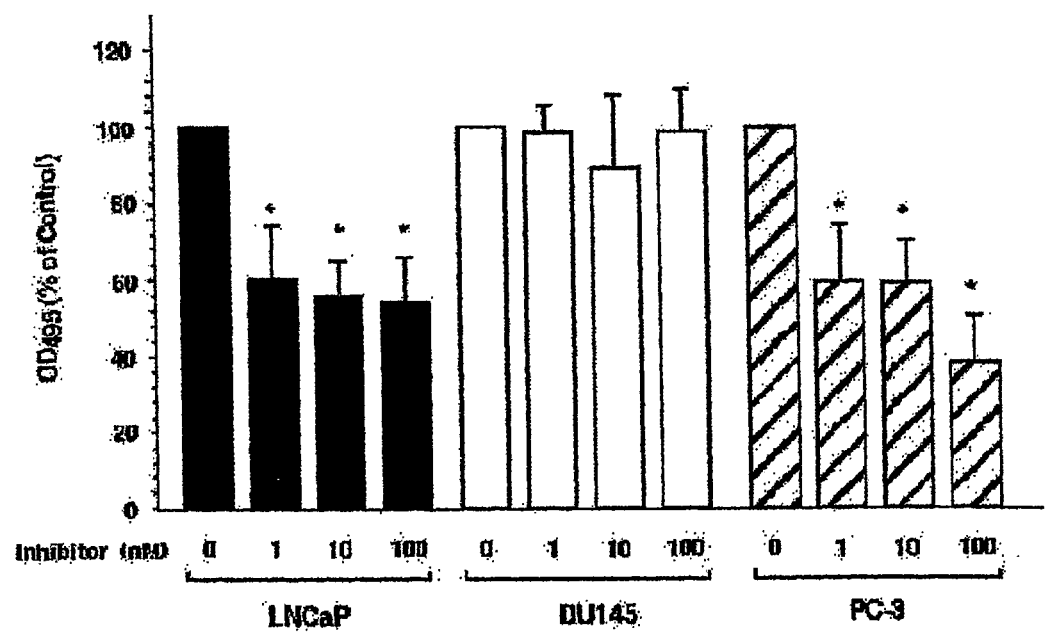

FIG. 4. Effect of sPLA$_2$-IIA inhibition on unstimulated prostate cancer cells. (A) The endogenous expression of sPLA$_2$-IIA mRNA was evaluated by RT-PCR in three unstimulated prostate cancer cell lines (LNCaP, DU145 and PC-3) grown in RPMI containing 5% FCS. HPRT was used to as a positive control for RNA integrity and loading. (B) Cells were grown in RPMI with 5% FCS were then treated for 72 hours in the presence and absence of the sPLA$_2$-IIA inhibitor c(2Nap)LS(2Nap)R and cell number determined by MTS assay as described in Materials and Methods. Data are mean±SD of quadruplicate determinations expressed as percentages relative to untreated control cells (100%). LNCaP, closed bars, $OD_{495}$ untreated cells 0.50±0.03; DU145, open bars, $OD_{495}$ untreated cells 0.73±0.05; PC-3, hatched bars, $OD_{495}$ untreated cells, 0.66±0.01. *p<0.05 vs untreated control by one-way ANOVA.

DETAILED DESCRIPTION OF THE INVENTION

Unless defined otherwise, all technical and scientific terms used herein have the same meaning as commonly understood by one of ordinary skill in the art (e.g. in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2nd ed. (1989) Cold Spring Harbor Laboratory Press, Cold Spring Harbor, N.Y. and Ausubel et al., Short Protocols in Molecular Biology (1999) 4th Ed, John Wiley & Sons, Inc.—and the full version entitled Current Protocols in Molecular Biology, which are incorporated herein by reference) and chemical methods.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

PLA$_2$ Enzymes

The methods of the present invention encompass targeting any PLA$_2$ enzyme. A review of the classification and characterisation of the expanding superfamily of PLA$_2$ enzymes had been published by Six and Dennis (2000) *Biochim. Biophys. Acta* 1488:1-19, and the present methods contemplate targeting all of these enzymes.

In preferred embodiments of the present invention, the PLA$_2$ enzyme is sPLA$_2$-IIA or cPLA$_2$-α. Preferably, the PLA$_2$ enzyme is a human enzyme.

The nucleic acid and protein sequences for human sPLA$_2$-IIA are shown in SEQ ID NOs:1 and 3 respectively. The nucleic acid and protein sequences for human cPLA$_2$-α are shown in SEQ ID NOs:2 and 4 respectively.

PLA$_2$ Inhibitors

Protein or Peptide inhibitors

In one embodiment, peptidyl PLA$_2$ inhibitors are chemically or recombinantly synthesized as oligopeptides (approximately 10-25 amino acids in length) derived from the a PLA$_2$ sequence (for example, SEQ ID NO:3 or 4). Alternatively, PLA$_2$ fragments are produced by digestion of native or recombinantly produced PLA$_2$ by, for example, using a protease, e.g., trypsin, thermolysin, chymotrypsin, or pepsin. Computer analysis (using commercially available software, e.g. MacVector, Omega, PCGene, Molecular Simulation, Inc.) is used to identify proteolytic cleavage sites. The proteolytic or synthetic fragments can comprise as many amino acid residues as are necessary to partially or completely inhibit PLA$_2$ function. Preferred fragments will comprise at least 5, 10, 15, 20, 25, 30, 35, 40, 45, 50, 55, 60, 65, 70, 75, 80, 85, 90, 95, 100 or more amino acids in length.

Protein or peptide inhibitors may also be dominant-negative mutants of PLA$_2$. The term "dominant-negative mutant" refers to a PLA$_2$ polypeptide that has been mutated from its natural state and that interacts with a protein that PLA$_2$ normally interacts with thereby preventing endogenous native PLA$_2$ from forming the interaction.

Anti-PLA$_2$ Antibodies

The term "antibody" as used in this invention includes intact molecules as well as fragments thereof, such as Fab, F(ab')2, and Fv which are capable of binding an epitopic determinant of PLA$_2$. These antibody fragments retain some ability to selectively bind with its antigen and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

Antibodies of the present invention can be prepared using intact PLA$_2$ or fragments thereof as the immunizing antigen.

A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide may then be used to immunize the animal (e.g., a mouse or a rabbit).

If desired, polyclonal antibodies can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

Monoclonal antibodies may be prepared using any technique which provides for the production of antibody molecules by continuous cell lines in culture, such as, for example, the hybridoma technique, the human B-cell hybridoma technique, and the EBV-hybridoma technique (Kohler et al. Nature 256, 495-497, 1975; Kozbor et al., J. Immunol. Methods 81, 3142, 1985; Cote et al., Proc. Natl. Acad. Sci. USA 80, 2026-2030, 1983; Cole et al., Mol. Cell Biol. 62, 109-120, 1984).

Methods known in the art allow antibodies exhibiting binding for $PLA_2$ to be identified and isolated from antibody expression libraries. For example, a method for the identification and isolation of an antibody binding domain which exhibits binding to $PLA_2$ is the bacterio-phage a vector system. This vector system has been used to express a combinatorial library of Fab fragments from the mouse antibody repertoire in *Escherichia coli* (Huse, et al., Science, 246:1275-1281, 1989) and from the human antibody repertoire (Mullinax, et al., Proc. Nat. Acad. Sci., 87:8095-8099, 1990). This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. Details of these techniques are described in such references as Monoclonal Antibodies-Hybridomas: A New Dimension in Biological Analysis, Edited by Roger H. Kennett, et al., Plenum Press, 1980; and U.S. Pat. No. 4,172,124, incorporated by reference.

In addition, methods of producing chimeric antibody molecules with various combinations of "humanized" antibodies are known in the art and include combining murine variable regions with human constant regions (Cabily, et al. Proc. Natl. Acad. Sci. USA, 81:3273, 1984), or by grafting the murine-antibody complementarity determining regions (CDRs) onto the human framework (Riechmann, et al., Nature 332:323, 1988).

Antisense Compounds

The term "antisense compounds" encompasses DNA or RNA molecules that are complementary to at least a portion of a $PLA_2$ mRNA molecule (Izant and Weintraub, Cell 36:1007-15; 1984; Izant and Weintraub, Science 229(4711): 345-52, 1985) and capable of interfering with a post-transcriptional event such as mRNA translation. Antisense oligomers complementary to at least about 15 contiguous nucleotides of $PLA_2$-encoding mRNA are preferred, since they are easily synthesized and are less likely to cause problems than larger molecules when introduced into the target $PLA_2$-producing cell. The use of antisense methods is well known in the art (Marcus-Sakura, Anal. Biochem. 172: 289, 1988). Preferred antisense nucleic acid will comprise a nucleotide sequence that is complementary to at least 15 contiguous nucleotides of a sequence encoding the amino acid sequence set forth in SEQ ID NO:3 or 4.

Catalytic Nucleic Acids

The term catalytic nucleic acid refers to a DNA molecule or DNA-containing molecule (also known in the art as a "DNAzyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T and U, as well as derivatives thereof. Derivatives of these bases are well known in the art.

Typically, the catalytic nucleic acid contains an antisense sequence for specific recognition of a target nucleic acid, and a nucleic acid cleaving enzymatic activity (also referred to herein as the "catalytic domain"). To achieve specificity, preferred ribozymes and DNAzymes will comprise a nucleotide sequence that is complementary to at least about 12-15 contiguous nucleotides of a sequence encoding the amino acid sequence set forth in SEQ ID NO:3 or 4.

The types of ribozymes that are particularly useful in this invention are the hammerhead ribozyme (Haseloff and Gerlach 1988, Perriman et al., 1992) and the hairpin ribozyme (Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for the ribozymes of this invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

RNA Inhibitors dsRNA is particularly useful for specifically inhibiting the production of a particular protein. Although not wishing to be limited by theory, Dougherty and Parks (1995) have provided a model for the mechanism by which dsRNA can be used to reduce protein production. This model has recently been modified and expanded by Waterhouse et al. (1998). This technology relies on the presence of dsRNA molecules that contain a sequence that is essentially identical to the mRNA of the gene of interest, in this case an mRNA encoding a $PLA_2$ protein. Conveniently, the dsRNA can be produced in a single open reading frame in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules targeted against $PLA_2$ is well within the capacity of a person skilled in the art, particularly considering Dougherty and Parks (1995), Waterhouse et al. (1998), WO 99/32619, WO 99/53050, WO 99/49029, and WO 01/34815.

As used herein, the terms "small interfering RNA", and "RNA" refer to homologous double stranded RNA (dsRNA) that specifically targets a gene product, thereby resulting in a null or hypomorphic phenotype. Specifically, the dsRNA comprises two short nucleotide sequences derived from the target RNA encoding $PLA_2$ and having self-complementarity such that they can anneal, and interfere with expression of a target gene, presumably at the post-transcriptional level. RNAi molecules are described by Fire et al., Nature 391, 806-811, 1998, and reviewed by Sharp, Genes & Development, 13, 139-141, 1999).

Small Molecule Inhibitors

Small molecule inhibitors that regulate $PLA_2$ are described in Lehr (2001) Expert Opin. Ther. Patents (2001) 11 (7):1123-1136, and Hansford et al (2003) Chem. Biochem. 4:181-185.

Peptides and Peptide Analogues

In preferred embodiments, the methods of the present invention involve the administration of conformationally constrained molecules derived from a peptide consisting essentially of amino acid residues 70 to 74 of a human $sPLA_2$-IIA protein, or the equivalent residues in other $sPLA_2$-IIA proteins.

In general, reference to amino acid residues 70 to 74 of the human $sPLA_2$-IIA protein is taken to include reference to the equivalent residues in other $sPLA_2$-IIA proteins, such as orthologues of human $sPLA_2$-IIA.

The term "conformationally constrained molecules" means conformationally constrained peptides and conformationally constrained peptide analogues and derivatives.

Thus the conformationally constrained molecules according to the present invention include conformationally constrained peptides consisting essentially of residues 70 to 74 of the human $sPLA_2$-IIA protein, and analogues and derivatives thereof.

The term "analogues" refers to molecules having a chemically analogous structure to the naturally occurring alpha-amino acids present as residues 70 to 74 of the human $sPLA_2$-IIA protein. Examples include molecules containing gem-diaminoalkyl groups or alkylmalonyl groups.

The term "derivatives" includes alpha amino acids wherein one or more side groups found in the naturally occurring alpha-amino acids present as residues 70 to 74 of human $sPLA_2$-IIA protein have been modified. Thus, for example the naturally-occurring amino acids present in residues 70 to 74 of the human $sPLA_2$-IIA protein may be replaced with a variety of uncoded or modified amino acids such as the corresponding D-amino acid or N-methyl amino acid. Other modifications include substitution of hydroxyl, thiol, amino and carboxyl functional groups with chemically similar groups.

The present invention encompasses the use of conformationally constrained peptidomimetics of the biologically active human $sPLA_2$-IIA peptide (amino acid residues 70 to), i.e. analogues and derivatives which mimic the activity of said peptide and are therefore capable of inhibiting the $sPLA_2$-IIA dependent proliferation of prostate cancer cells. These peptidomimetics are preferably substantially similar in both three-dimensional shape and biological activity to the specific $sPLA_2$-IIA peptides described herein. Substantial similarity means that the geometric relationship of groups in the peptide that react with the $sPLA_2$-IIA enzyme is preserved and at the same time, that the peptidomimetic will inhibit the $sPLA_2$-IIA dependent proliferation of prostate cancer cells.

A peptidomimetic is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics for use in the methods of the invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

There are clear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are much cheaper to produce than peptides.

Suitable peptidomimetics based on residues 70 to 74 of human $sPLA_2$-IIA peptides and having similar biological activities, and therefore similar therapeutic utilities, can be developed using readily available techniques. Thus, for example, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics derived from $sPLA_2$-IIA peptides based on residues 70 to 74 of human $sPLA_2$-IIA can be aided by determining the tertiary structure of the original peptide by NMR spectroscopy, crystallography and/or computer-aided molecular modelling. These techniques aid in the development of analogues/derivatives of higher potency and/or greater bioavailability and/or greater stability than the original peptide (Dean, 1994, BioEssays, 16: 683-487; Cohen and Shatzmiller, 1993, J. Mol. Graph., 11: 166-173; Wiley and Rich, 1993, Med. Res. Rev., 13: 327-384; Moore, 1994, Trends Pharmacol. Sci., 15: 124-129; Hruby, 1993, Biopolymers, 33: 1073-1082; Bugg et al., 1993, Sci. Am., 269: 92-98.

Information on the structure of an $sPLA_2$-IIA peptide consisting essentially of residues 70 to 74 of human $sPLA_2$-IIA can be used to search three-dimensional databases to identify molecules having a similar structure, using programs such as MACCS-3D and ISIS/3D (Molecular Design Ltd., San Leandro, Calif.), ChemDBS-3D (Chemical Design Ltd., Oxford, U.K.), and Sybyl/3DB Unity (Tripos Associates, St. Louis, Mo.).

Databases of chemical structures are available from a number of sources including Cambridge Crystallographic Data Centre (Cambridge, U.K), Chemical Abstracts Service (Columbus, Ohio), and ACD-3D (Molecular Design Ltd).

De novo design programs include Ludi (Accelrys), Leapfrog (Tripos Associates) and Aladdin (Daylight Chemical Information Systems, Irvine, Calif.).

Those skilled in the art will recognize that the design of a mimetic may require slight structural alteration or adjustment of a chemical structure designed or identified using these databases.

Peptide derivatives and peptidomimetic compounds based on amino acid residues 70 to 74 of human $sPLA_2$-IIA can be tested to determine whether they are capable of inhibiting sPLA$_2$-IIA dependent proliferation of prostate cancer cells using the assay described herein. Preferred peptide derivatives and peptidomimetics have at least 90%, preferably at least the same anti-proliferative activity toward prostate cancer cells as cFLSYR. It is also preferred that peptide derivatives and peptidomimetics specifically inhibit sPLA$_2$-IIA.

The molecules, such as peptides, used in the methods of the present invention are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of a peptide may be stabilized by a covalent modification, such as cyclization or by incorporation of gamma-lactam or other types of bridges. For example, side chains can be cyclized to the backbone so as create a L-gamma-lactam moiety on each side of the interaction site. See, generally, Hruby et al., 1992, "Applications of Synthetic Peptides," in Synthetic Peptides: A User's Guide: 259-345 (W. H. Freeman & Co.). Cyclization also can be achieved, for example, by formation of cystine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a polypeptide with the epsilon-amino group of a lysine residue, using iodoacetic anhydride, can be also undertaken. See, for example, Wood and Wetzel, 1992, *Int'l J. Peptide Protein Res.* 39: 533-39.

Another approach described in U.S. Pat. No. 5,891,418 is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino.

A further approach is to use bifunctional crosslinkers, such as N-succinimidyl 3-(2 pyridyidithio) propionate, succinimidyl 6-[3-(2 pyridyldithio) propionamido]hexanoate; and sulfosuccinimidyl 6-[3-(2 pyridyldithio) propionamido]hexanoate (see U.S. Pat. No. 5,580,853).

Techniques for chemically synthesising the peptides and derivatives described above are described in the above references and also reviewed by Borgia and Fields, 2000, *TibTech* 18: 243-251 and described in detail in the references contained therein.

Diagnostic Methods

The present invention also encompasses nucleic acid-based methods and protein-based methods for diagnosing prostate cancer in humans and other mammals.

As used herein, the term "diagnosis", and variants thereof, such as, but not limited to "diagnose", "diagnosed" or "diagnosing" shall not be limited to a primary diagnosis of a clinical state, however should be taken to include any primary diagnosis or prognosis of a clinical state. For example, the "diagnostic assay" formats described herein are equally relevant to assessing the remission of a patient, or monitoring disease recurrence, or tumor recurrence, such as following surgery or chemotherapy, or determining the appearance of metastases of a primary tumor. All such uses of the assays described herein are encompassed by the present invention.

Accordingly, the level of PLA$_2$ expression, at either the RNA level or the protein level, can be used to diagnose prostate cancer, or as a prognostic to monitor the progress of prostate cancer.

Preferred nucleic acid-based diagnostic assays rely upon the detection or relative quantification of RNA levels in samples using probes of at least about 20 nucleotides in length that hybridize specifically to RNA encoding PLA$_2$, or alternatively, amplify cDNA from RNA encoding PLA$_2$. Conveniently, any hybridization assay format can be used to detect PLA$_2$-encoding RNA in samples, such as, for example, high-throughput screening using microarray technology, or conventional northern hybridization or reverse transcription polymerase chain reaction (i.e. RT-PCR). In situ localization can also be employed using histology specimens.

Suitable diagnostic immunoassays utilize antibodies, including monoclonal and polyclonal antibodies, or a Fab fragment, F(ab')2 fragment, or scFv fragment, that binds to a unique peptide region comprising at least about 5-10 contiguous amino acid residues of PLA$_2$.

The present invention further encompasses any synthetic or recombinant peptides, or antibodies suitable for use in the assays described herein.

In preferred embodiments of these diagnostic methods the PLA$_2$ is sPLA$_2$-IIA or cPLA$_2$-α.

In another aspect, the invention relates to methods of diagnosing for predisposition to prostate cancer.

Accordingly, in one aspect the present invention provides a method of assessing the predisposition of a subject to prostate cancer, the method comprising the step of determining the presence of a polymorphism or an epigenetic change in a PLA$_2$ gene of the subject.

In one embodiment, the polymorphism is a PLA$_2$ polymorphism already identified in a public or private database such as the NCBI database or the Celera database.

The present invention encompasses nucleic-acid based methods and protein-based methods for diagnosing susceptibility to prostate cancer.

The polymorphism in the PLA$_2$ gene may be a point mutation (i.e. a single nucleotide polymorphism (SNP)), deletion and/or insertion. Such a polymorphism may be detected by isolating and sequencing DNA fragments from the PLA$_2$ gene or otherwise by isolating mRNA from the individual and synthesising DNA therefrom (e.g. by RT-PCR) for sequencing. Polymorphisms may also be detected by hybridisation using discriminating oligonucleotide probes or by amplification procedures using discriminating oligonucleotide primers. Suitable methods may involve Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; exon trapping, single base extension (SBE); or analysis of a PLA$_2$ protein.

In one embodiment the epigenetic change is aberrant methylation in a PLA$_2$ gene of the subject or insertion of an endogenous retroviral promoter or transposable element promoter close to a PLA$_2$ gene of the subject.

Methods of Screening for Therapeutic Agents

Also encompassed by the present invention are methods of identifying therapeutic agents useful for the treatment of prostate cancer.

Accordingly, in a first aspect the present invention provides a method of screening for a compound that reduces or inhibits the proliferation of prostate cells, the method comprising determining the activity of $PLA_2$ in the presence and absence of a candidate compound, wherein reduced $PLA_2$ activity in the presence of the compound indicates that the compound reduces or inhibits the proliferation of prostate cells.

In another aspect, the present invention provides a method of screening for a compound that reduces or inhibits the proliferation of prostate cells, the method comprising determining the expression levels of $PLA_2$ in the presence and absence of a candidate compound, wherein reduced $PLA_2$ expression in the presence of the compound indicates that the compound reduces or inhibits the proliferation of prostate cells.

In a further embodiment of this aspect, the method involves exposing a translation system capable of expressing $PLA_2$ to a candidate compound and comparing the levels of expression of $PLA_2$ in the presence of the compound to the levels achieved under similar conditions but in the absence of the compound. The translation system may be a cell-free translation system. Alternatively, the translation system may comprise eukaryotic or prokaryotic cells.

In a further aspect the present invention provides a method of screening for a compound that reduces or inhibits the proliferation of prostate cells, the method comprising determining the ability of a candidate compound to modulate the binding of $PLA_2$ to a $PLA_2$ substrate, wherein an altered level of binding of $PLA_2$ to the substrate in the presence of the compound indicates that the compound reduces or inhibits the proliferation of prostate cells.

In preferred embodiments of these screening methods the $PLA_2$ is $sPLA_2$-IIA or $cPLA_2$-$\alpha$.

Therapeutic Methods

We have shown that administration of exogenous $sPLA_2$-IIA to prostate cells stimulates cell proliferation. We have also shown that administration of $PLA_2$ inhibitors inhibits $sPLA_2$-IIA mediated cell proliferation. Consequently, $PLA_2$ inhibitors can be used to inhibit or reduce prostate cell proliferation in cells, particularly in cells with elevated sPLA-IIA activity such as prostate cancer cells.

The $PLA_2$ inhibitors can be used therapeutically for prostate cancers, particularly AIPCs. The term "therapeutically" or as used herein denotes both prophylactic as well as therapeutic administration. Thus, $PLA_2$ inhibitors can be administered to high-risk patients in order to lessen the likelihood and/or severity of prostate cancer or administered to patients already evidencing prostate cancer.

The peptides, analogues and small molecule inhibitors described above may preferably be combined with various components to produce compositions. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline, water, dry powders and micelles. The composition may be administered by any means known in the art. Modes of delivery include, but are not limited to, direct injection, topical delivery (e.g. by atomised nasal delivery or nasal drops) or oral delivery. Accordingly, the composition may be formulated, inter alia, for topical, parenteral, intramuscular, intravenous, subcutaneous, intraocular, oral or transdermal administration.

Typically, each peptide or analogue or derivative thereof may be administered at a dose of from 0.01 to 30 mg/kg body weight, preferably from 0.1 to 10 mg/kg, more preferably from 0.1 to 1 mg/kg body weight.

The routes of administration and dosages described are intended only as a guide since a skilled practitioner will be able to determine readily the optimum route of administration and dosage for any particular patient and condition.

The present invention will now be described further with reference to the following examples which are intended to be illustrative only and non-limiting.

EXAMPLES

Materials and Methods

Cell Lines and Culture. The LNCaP, DU145 and PC3 cell lines were purchased from American Type Culture Collection (Rockville, Md.). All cell cultures were maintained in RPMI 1640 supplemented with 5% FBS for LNCaP and 10% FBS for DU145 and PC3 at 37° C. in a humidified environment of 5% $CO_2$. For experiments with addition of androgens, cells were cultured in RPMI 1640 without phenol red and supplemented with same concentration of charcoal stripped FBS. For experiments described in this article, we used cells between passage 30 and 45 for LNCaP, 65 and 80 for DU145 and 25 and 40 for PC3.

Reagents. $sPLA_2$-IIA was purified by immunoaffinity chromatography from conditioned media derived from Chinese hamster ovary cell line (5A2) expressing human $sPLA_2$-IIA as described (Bidgood, M. J. et al. J. Immunol. (2000) 165:2790-2797). A cDNA encoding the activity-dead mutant $sPLA_2$-IIA $H_{48}Q$ was constructed by oligonucleotide-mediated site-directed mutagenesis using standard molecular techniques. This cDNA was expressed in Chinese hamster ovary cells under the control of the human metallothionein promoter.

$H_{48}Q$ was purified from conditioned media derived from this cell line by immunoaffinity chromatography. Purity was verified by the presence of a single band on a silver-stained SDS gel and by amino terminal peptide sequence analysis. Enzyme activity was undetectable in the purified protein as determined by the radiolabelled *Eschericia coli* assay (Church, W. B. et al. (2001), J. Biol. Chem. 276:33156-33164). Both mutant protein and $sPLA_2$-IIA were quantified by ELISA (Smith, G. M. et al., Br. J. Rheumatol. (1992) 31: 175). $sPLA_2$-IIA inhibitors (Church, W. B. et al) were synthesized using Fmoc (N-(9-fluoroenyl)methoxycarbonyl) solid phase chemistry without removal of side-chain protection groups prior to cleavage from the resin. Peptides were cyclised using standard peptide synthesis activation and coupling chemistry prior to deprotection (Auspep, Melbourne). The $cPLA_2$ inhibitor pyrrolidone-1 was a kind gift from Dr Michael Gelb.

Antibodies used in these experiments included polyclonal anti-$sPLA_2$-IIa (160502, Cayman Chemicals, monoclonal anti-$sPLA_2$-IIA antibody 4A1 raised by ourselves (Smith, G. M. et al.), and anti-$cPLA_2$ polyclonal antibody (SC-438, Santa Cruz).

Cell growth assay. Cells were plated at $1 \times 10^4$ per well in 96-well plates with 0.1 ml of FBS-supplemented RPMI. After reaching 70-80% confluence (about 48 hours), the medium was changed to that containing various treatments for 3 days. After treatment, the number of viable cells was determined using the MTS assay (CellTiter 96® AQueous Assay; Promega, Madison, Wis.). In brief, 20 ul of MTS solution was added to each well and cells were incubated for 1 h. The absorbance at 490 nm was measured with an ELISA microplate reader. Each experiment was performed in quadruplicate and repeated at least three times.

Flow Cytometric Analysis. Cells were seeded in 25 ml flasks in conditions as described above. Following treatment, trypsinization and cell counting, LNCaP cells ($1 \times 10^6$) were suspended in 1 mL PBS and incubated with 0.2 mL 0.4% Triton® X-100 for 5 min at R/T in the presence of 50 µL of propidium iodide solution (50 µg/mL) and 20 µL of ribonuclease (10 mg/mL). DNA content per cell was measured by flow cytometry using an FACScalibur® flow cytometer and CellQuest® software (Becton Dickinson, Franklin Lakes, N.J.). Statistical analysis was performed on 10,000 events per sample.

RT-PCR. Total cellular RNA was isolated from LNCaP, DU145 or PC-3 cells using the Trizol® reagent (LifeTechnologies, Inc.). First-strand cDNA was synthesized from 5 µg of RNA with the cDNA preamplification system (Life Technologies, Inc.) using SuperScript® II reverse transcriptase and an oligo(dT) primer. This was used as the template in standard PCR reactions using Amplitaq® DNA polymerase (Perkin-Elmer Life Sciences, Boston, Mass.). Amplification products were analyzed on 2% TAE agarose gels made with MetaPhor® agarose (FMC BioProducts, Rockland, Me.) and photographed under UV illumination. DNA ladders of 25 and 100 by (Life Technologies, Inc.) were used as size standards. Primers were designed based on the human $sPLA_2$-IIA mRNA (NM_000300.2) deposited in the GenBank database (National Center for Biotechnology Information, Bethesda, Md.) and are as follows:

```
forward:    5'-TTTGTCACCCAAGAACTCTTAC-3', reverse:    5'-GGGAGGGAGGGTATGAGA-3'.
```

Tissues. Normal prostate was obtained from brain-dead organ donors as described previously (Chetcuti et al., (2001) Cancer Research, 61:6331-6334). Benign prostatic hyperplasia (BPH) was obtained from transurethral resection of the prostate. Cancer tissue was from radical prostatectomy. Informed consent was obtained from patients, and the study protocol was approved by the Central Sydney Area Health Service Ethics Review Committee.

Immunohistochemistry. Prostate tissues (normal, benign hyperplastic and cancer) were all fixed in 10% formaldehyde solution for <24 hours and paraffin embedded. Tissue sections (5 µm) were incubated for 1 hour at 37° C. after microwave antigen retrieval with the appropriate primary antibody diluted in 1% oat serum. Biotinylated goat anti-rabbit or mouse IgG, diluted 1/200 in 1% normal goat serum, was used as the secondary antibody. The signal was amplified using the avidin-biotin-peroxidase complex system (Vector Laboratories) and visualised using the liquid DAB substrate-chromogen system (Dako). Sections were counterstained with hematoxylin. Negative isotype and method controls were performed for each sample by substituting the primary antibody with rabbit IgG and 1% goat serum, respectively.

Image Analysis. Immunoperoxidase staining was considered positive and specific when the intensity of with the post-immune IgG clearly exceeded that observed with the preimmune IgG (isotype control) and with no IgG (method control). Specific staining was graded for the percentage of immunopositive normal or cancer epithelial cells as described (Kommoss, 1989 Anal. Quant. Cytol. Histol. 11:298-306). Briefly, the percentage of positive-stained normal, or cancerous epithelial cells per slide was stratified into three groups: group 1, 0-33%; group 2, 34-66%; and group 3, 67-100%. Zero represented no cells with specific staining.

Statistical Analysis. The Number Cruncher Statistical System (NCSS, Kaysville, Utah) was used for statistical analysis. Data were analyzed by one-way ANOVA and correlation coefficient as appropriate. A two-tailed P value <0.05 was considered significant.

Example 1

Figure 1:
FIG. 1. Effect of androgen ablation therapy on sPLA$_2$-IIA protein expression. Prostate tissue from patients following radical prostatectomy either with (N=25) or without (N=50) prior androgen ablation therapy were examined for sPLA$_2$-IIA protein expression by immunohistochemistry as described in Materials and Methods. A. Adjacent sections from a patient without androgen-ablation therapy showing normal glands. B. Adjacent sections from a patient following androgen ablation therapy showing both normal and neoplastic tissue. Left panel stained with haematoxilin and eosin, right panel stained with anti-sPLA$_2$-IIA antibody. Magnification, ×40. C. sPLA$_2$-IIA expression in normal (open boxes) or neoplastic (closed boxes) tissue from patients with (+) or without (−) androgen ablation therapy was graded on a 3-point score, (1; 0-33% tissue positive, 2; 33-66% tissue positive and 3; >66% tissue positive). *; P<0.05 vs no androgen ablation therapy treated benign glands by Chi-Square analysis.
Figure 1:
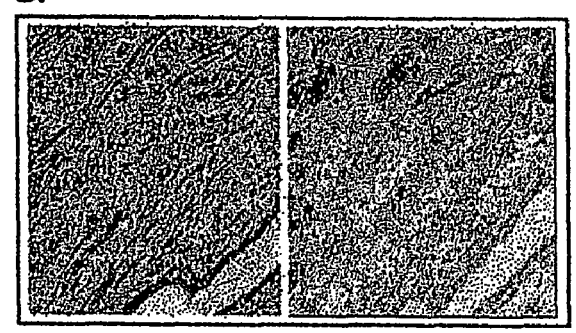
Figure 1:
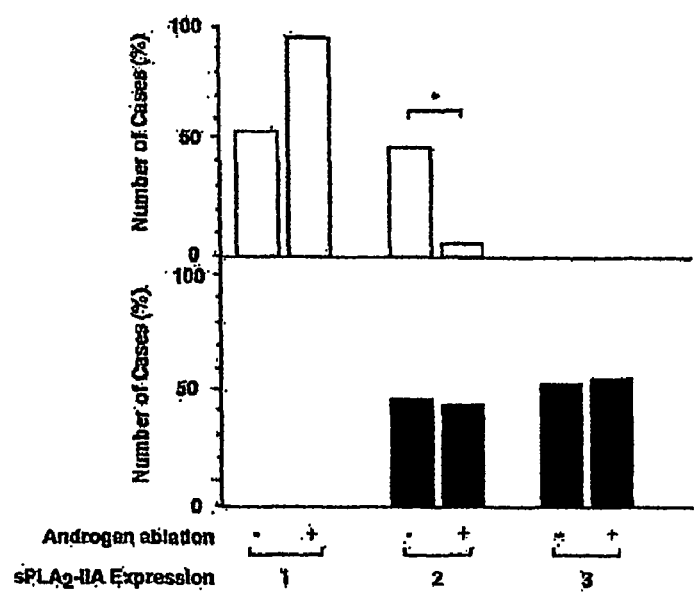

$sPLA_2$-IIA is Induced in Prostate Cancer Cells and Constitutively Activated in AIPC We searched the database of Serial Analysis of Gene Expression (SAGE) to determine the steady state mRNA levels of individual $PLA_2$ enzymes in prostate cancer. The cDNA libraries used for SAGE was PR317 normal prostate and PR317 prostate cancer, respectively, as both are derived from microdissected prostate tissues. We found that $sPLA_2$-IIA mRNA was 22 times higher in prostate cancer than normal prostate, whereas other members were either not expressed in the prostate libraries or unchanged in cancer. To verify the SAGE result and extend the expression analysis to androgen-independent prostate cancer (AIPC), we examined $sPLA_2$-IIA expression by immunohistochemistry in prostate cancer tissues from patients treated with androgen-ablation therapy for 3 months prior to radical prostatectomy. Cancer cells remaining in specimens following androgen-ablation therapy are regarded as being closest to AIPC, although they are confined within the prostate. Cancer specimens from patients undergoing radical prostatectomy without androgen ablation therapy served as the control. Two antibodies were used for immunohistochemistry, and both showed the same expression pattern. In the control group, (N=50), there was weak and patchy staining in benign glands (FIGS. 1A and C.) adjacent to cancer cells and extensive staining in cancer cells (FIG. 1C.). In the androgen-ablated group (N=25), benign glands lost their staining, whereas AIPC cells maintained $sPLA_2$-IIA expression (FIGS. 1B and C). We also found that the extent of $sPLA_2$-IIA staining is positively correlated with the tumour grade and post-operative PSA level (data not shown). The chromosomal location of $sPLA_2$-IIA (1p35.1-36) was also found to overlap with a prostate cancer susceptibility locus CAPB (Gibbs et al (1999) Am. J. Hum. Genet. 64:776-787). No difference was found in immunohistochemical staining for $cPLA_2$-α between normal and cancer cells irrespective of androgen status (data not shown).

The lack of $sPLA_2$-IIA expression in benign glands following androgen deprivation suggests that expression of $sPLA_2$-IIA gene requires androgens. To verify that, we searched the 5'-flanking region of the $sPLA_2$-IIA gene using MatInspector Release 5.3 (Genomatix), and found an androgen response element (ARE) GAGGTAAATGGTATTCTC (SEQ ID NO: 9) from -546 to -527. Secondly, we treated the androgen responsive human prostate cancer cell line, LNCaP, with various doses of androgens and measured $sPLA_2$-IIA mRNA and protein levels by RT-PCR and ELISA (data not shown). Indeed, there was an increase in the level of $sPLA_2$-IIA transcript following 1 nM androgen treatment. In contrast, we could not find an ARE within 3 kb of genomic DNA in the 5-flanking region of the $cPLA_2$-α gene. Androgen treatment had no effect on $cPLA_2$-α mRNA and protein levels (data not shown). Together, these findings indicate that $sPLA_2$-IIA, but not $cPLA_2$-α expression is normally dependent on androgens and in AIPC sPLA$_2$-IIA expression becomes androgen-independent via an as yet unknown mechanism.

Example 2

Oncogenic Action of sPLA$_2$-IIA in Prostate Cancer Cells

Figure 2:
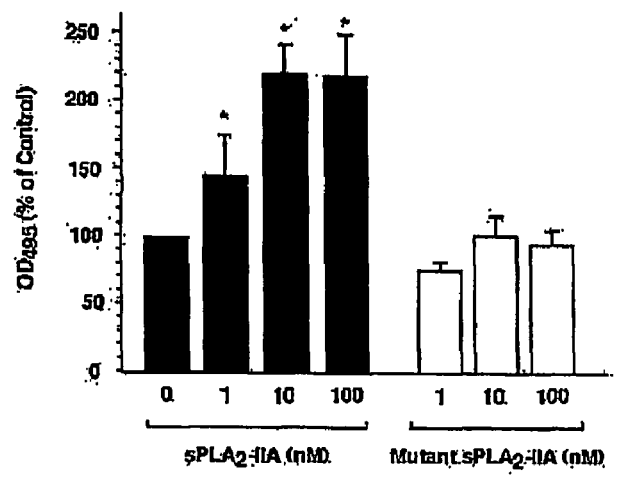
FIG. 2. Effect of exogenous addition of sPLA$_2$-IIA on prostate cell growth. LNCaP cells were grown in RPMI with 5% FCS and treated for 72 hours in media containing (A) increasing concentrations of sPLA$_2$-IIA alone (closed bars) or increasing concentrations of the activity-dead sPLA$_2$-IIA mutant H$_{48}$Q. (B) a fixed concentration of sPLA2-IIA and increasing concentrations of the sPLA$_2$-IIA inhibitor cFLSYR (SEQ ID NO: 6). Cell number relative to untreated control cells was determined by the MTS assay as described in Materials and Methods. Data are Mean±SD of quadruplicate determinations normalised to 100% for untreated cells.
Figure 2:
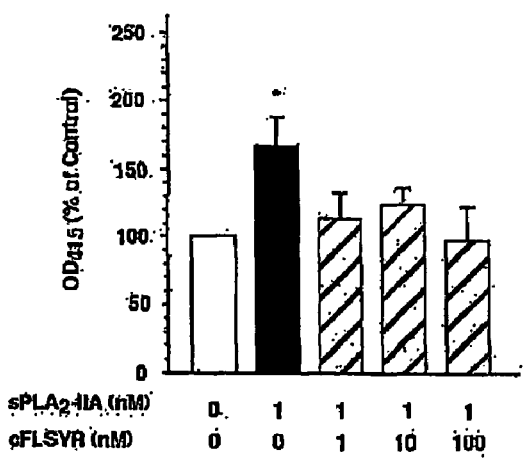
Figure 2:
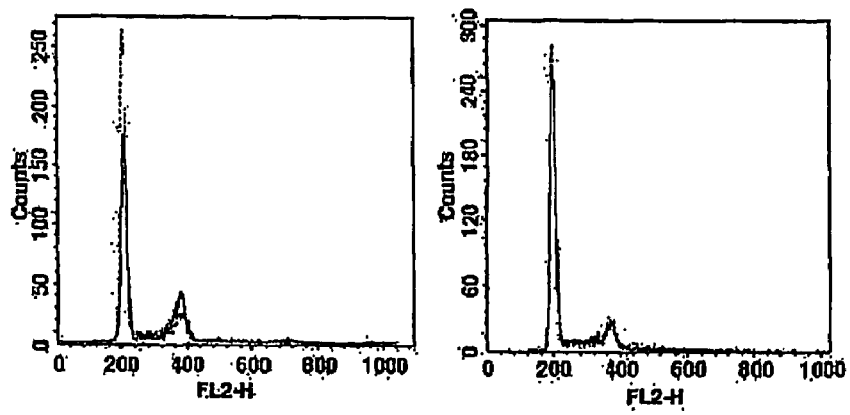

To examine the biological relevance of sPLA$_2$-IIA to prostate cancer cell growth, we treated LNCaP cells with increasing doses of human recombinant sPLA$_2$-IIA and monitored cell growth. LNCaP is the only available prostate cancer cell line that expresses both the androgen receptor and PSA. Exogenously-added sPLA$_2$-IIA at doses as low as 1 nM, consistently and dose-dependently stimulated LNCaP cell growth as measured by the 3-(4,5-dimethylthiazol-2-yl)-5-(3-carboxymethylphenyl)-2-(4-sulphophenyl)-2H-tetrazolium (MTS) assay (FIG. 2A). In contrast addition of an activity-dead sPLA$_2$-IIA mutant protein H$_{48}$Q, showed no stimulation relative to untreated cells (FIG. 2A) indicating that enzyme activity is essential for the growth-stimulatory effect.

We have previously shown that human sPLA$_2$-IIA is dose-dependently inhibited by a pentapeptide sequence comprising residues 70-74 of the native sPLA$_2$-IIA protein ($^{70}$FLSKY$^{74}$) SEQ ID NO:5 (Tseng, A., et al., (1996) J. Biol. Chem. 271:23992-23998). Because of the inherent flexibility of the linear peptide sequence, inhibition was weak in in vitro activity assays. We have recently designed two novel cyclic peptides (Church, W. B. et al.), cFLSYR (SEQ ID NO: 6) and a cyclic peptide where F and Y are substituted with 2-naphthylalanine (c(2NapA)LS(2NapA)R). Both have shown significant improvement in potency over linear peptides. The potent stimulatory effect of exogenous sPLA$_2$-IIA on prostate cancer cell number was completely blocked by the sPLA$_2$-IIA inhibitor, cFLSYR (SEQ ID NO: 6) (FIG. 2B) at all concentrations tested.

We next used flow cytometric analysis to determine how sPLA$_2$-IIA affects the distribution of LNCaP cells in different phases of the cell cycle. In sPLA$_2$-IIA containing medium, the proportion of LNCaP cells in the G1 phase decreased from 74% to 62% with corresponding increase of cells in G2/M phase in comparison to untreated cells (FIG. 2C). In the presence of both sPLA$_2$-IIA and its inhibitor (cFLSYR) (SEQ ID NO: 6), the proportion of cells in G1 and G2 phase returned to basal levels (FIG. 2C). These results establish the biological importance of the sPLA$_2$-IIA enzyme activity in prostate cancer cells and demonstrate that sPLA$_2$-IIA-induced cell growth can be attributed at least partly to an increased proportion of cells entering G2/M phase from G1 phase.

Example 3

Oncogenic Action of sPLA$_2$-IIA Requires cPLA$_2$-α Activity

Currently, two models are proposed to explain the action of sPLA$_2$ on eicosanoid production (Murakami, M., Kudo, I. (2002) J. Biochem. 131:285-292). One is the direct cleavage of membrane phospholipids. In this model, sPLA$_2$ binds directly to plasma membrane phospholipids and the released arachidonic acid serves as a substrate to produce eicosanoids. Lysophospholipids and/or eicosanoid products of arachidonic acid metabolism mediate indirect activation of the endogenous cPLA$_2$-α via mobilisation of calcium. The enhanced cPLA$_2$-α activity can in turn result in enhanced production of eicosanoids. The second model is indirect modulation of intracellular eicosanoid pathways via cell surface GPI-linked heparan sulphate proteoglycan receptors. The internalised sPLA$_2$ supplies arachidonic acid to downstream enzymes either directly, or indirectly via activation of cPLA$_2$-α through mitogen activated protein (MAP) kinase-mediated phosphorylation.

To determine if sPLA$_2$-IIA-induced cell proliferation depends on cPLA$_2$-α, we treated LNCaP cells with various doses of selective cPLA$_2$ inhibitor, pyrrolidine-1 (Ghomashchi, F. et al. (2001) Biochim. Biophys. Acta Biomembranes 2:160-166) with or without a constant effective dose of sPLA$_2$-IIA (1 nM). Blockade of cPLA$_2$-α abolishes sPLA$_2$-IIA-induced cell growth completely (FIG. 3), demonstrating that cPLA$_2$-α activation is necessary for sPLA$_2$-IIA-dependent cell proliferation. In the absence of sPLA$_2$-IIA, the cPLA$_2$-α inhibitor had no effect on cell growth, suggesting that cPLA$_2$-α does not promote cell proliferation independently in LNCaP cells (see legend FIG. 3).

Example 4 sPLA$_2$-IIA Inhibitors Suppress Endogenous Proliferation

Based on our finding that the growth-promoting sPLA$_2$-IIA is constitutively expressed in AIPC we have considered the potential of sPLA$_2$-IIA as a target for treatment of AIPC. We reason that a better outcome can be achieved with the PLA$_2$ inhibitor than with a COX inhibitor alone because the latter suppresses the production of prostaglandins only.

To test the effect of blocking endogenous sPLA$_2$-IIA on cell growth, we firstly determined the basal mRNA levels of sPLA$_2$-IIA in 3 human prostate cancer cell lines. The androgen-independent cell lines PC-3 and DU145 cells were included in the study to also exclude a possible general toxicity of the inhibitors. mRNA encoding sPLA$_2$-IIA was undetectable in DU-145 compared with LNCaP and PC-3 cells (FIG. 4A). We then tested the effect of individual inhibitors cFLSYR (SEQ ID NO: 6) and c(2Nap)LS(2Nap) R on cell growth over a range of doses (1-100 nM). The proliferation of LNCaP and PC-3 cells was significantly decreased, and the smallest effective dose was 1 nM for both inhibitors (FIG. 4B). In contrast, neither of the inhibitors had an effect on DU145, presumably due to the lack of endogenous sPLA$_2$-IIA. The low but effective dosage and its specificity for cell lines containing endogenous sPLA$_2$-IIA only, indicate that non-specific cell toxicity is not likely to explain the inhibitory effect.

In summary, the normally androgen-induced sPLA$_2$-IIA gene expression is constitutively activated in androgen-independent prostate cancer. Exogenously added sPLA$_2$-IIA promotes prostate cell proliferation through its enzyme product and cPLA$_2$. A better therapeutic outcome is likely to be achieved with an sPLA$_2$ inhibitor in prostate cancer including the form of AIPC.

All publications mentioned in the above specification are herein incorporated in their entirety by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the invention.

The invention claimed is:

1. A method of inhibiting or reducing the proliferation of prostate cancer cells that express a sPLA$_2$-IIA polypeptide comprising the amino acid sequence of SEQ ID NO: 3 in a human subject who has been subjected to androgen ablation therapy, the method comprising administering to the subject a selective inhibitor of the enzyme activity of the polypeptide, wherein the inhibitor inhibits the ability of the polypeptide to catalyse the hydrolysis of membrane phospholipids at the sn-2 position to release fatty acids and lysophospholipids, wherein the inhibitor inhibits the sPLA$_2$-IIA-mediated proliferation of prostate cancer cells, and wherein the inhibitor is a cyclic peptide of the following formula:

A1-A2-A3-A4-A5, in which

A1 is F or Y or W or 2Nap
A2 is L or I
A3 is S or T
A4 is F or Y or W or 2Nap, and
A5 is R or K.

2. A method according to claim 1 wherein the prostate cancer cells are androgen independent prostate cancer (AIPC) cells.

3. A method according to claim 1, wherein the peptide is selected from the group consisting of cFLSYK (SEQ ID NO:5), cFLSYR (SEQ ID NO:6) and c(2NapA)LS(2NapA)R.

* * * * *

SEQUENCE LISTING

<160> NUMBER OF SEQ ID NOS: 9

<210> SEQ ID NO 1
<211> LENGTH: 997
<212> TYPE: DNA
<213> ORGANISM: Homo sapiens

<400> SEQUENCE: 1

| | | | | | | |
|---|---|---|---|---|---|---|
| gaaggaaaaa | gagcaacaga | tccagggagc | attcacctgc | cctgtctcca | aacagccttg | 60 |
| tgcctcacct | accccaacc | tcccagaggg | agcagctatt | taaggggagc | aggagtgcag | 120 |
| aacaaacaag | acggcctggg | gatacaactc | tggagtcctc | tgagagagcc | accaaggagg | 180 |
| agcaggggag | cgacggccgg | ggcagaagtt | gagaccaccc | agcagaggag | ctaggccagt | 240 |
| ccatctgcat | ttgtcaccca | agaactctta | ccatgaagac | cctcctactg | ttggcagtga | 300 |
| tcatgatctt | tggcctactg | caggcccatg | ggaatttggt | gaatttccac | agaatgatca | 360 |
| agttgacgac | aggaaaggaa | gccgcactca | gttatggctt | ctacggctgc | cactgtggcg | 420 |
| tgggtggcag | aggatccccc | aaggatgcaa | cggatcgctg | ctgtgtcact | catgactgtt | 480 |
| gctacaaacg | tctggagaaa | cgtggatgtg | gcaccaaatt | tctgagctac | aagtttagca | 540 |
| actcggggag | cagaatcacc | tgtgcaaaac | aggactcctg | cagaagtcaa | ctgtgtgagt | 600 |
| gtgataaggc | tgctgccacc | tgttttgcta | gaaacaagac | gacctacaat | aaaaagtacc | 660 |
| agtactattc | caataaacac | tgcagaggga | gcacccctcg | ttgctgagtc | ccctcttccc | 720 |
| tggaaacctt | ccacccagtg | ctgaatttcc | ctctctcata | ccctccctcc | ctaccctaac | 780 |
| caagttcctt | ggccatgcag | aaagcatccc | tcacccatcc | tagaggccag | gcaggagccc | 840 |
| ttctataccc | acccagaatg | agacatccag | cagatttcca | gccttctact | gctctcctcc | 900 |
| acctcaactc | cgtgcttaac | caagaagct | gtactccggg | gggtctcttc | tgaataaagc | 960 |
| aattagcaaa | aaaaaaaaa | aaaaaaaaaa | aaaaaaa | | | 997 |

<210> SEQ ID NO 2
<211> LENGTH: 2875
<212> TYPE: DNA
<213> ORGANISM: Homo sapiens

<400> SEQUENCE: 2

| | | | | | | |
|---|---|---|---|---|---|---|
| gaattctccg | gagctgaaaa | aggatcctga | ctgaaagcta | gaggcattga | ggagcctgaa | 60 |
| gattctcagg | ttttaaagac | gctagagtgc | caaagaagac | tttgaagtgt | gaaacatttt | 120 |
| cctgtaattg | aaaccaaaat | gtcatttata | gatccttacc | agcacattat | agtggagcac | 180 |
| cagtattccc | acaagtttac | ggtagtggtg | ttacgtgcca | ccaaagtgac | aaaggggggcc | 240 |
| tttggtgaca | tgcttgatac | tccagatccc | tatgtggaac | tttttatctc | tacaaccccct | 300 |
| gacagcagga | agagaacaag | acatttcaat | aatgacataa | accctgtgtg | gaatgagacc | 360 |
| tttgaattta | ttttggatcc | taatcaggaa | aatgttttgg | agattacgtt | aatggatgcc | 420 |
| aattatgtca | tggatgaaac | tctagggaca | gcaacattta | ctgtatcttc | tatgaaggtg | 480 |
| ggagaaaaga | aagaagttcc | ttttatttc | aaccaagtca | ctgaaatggt | tctagaaatg | 540 |
| tctcttgaag | tttgctcatg | cccagaccta | cgatttagta | tggctctgtg | tgatcaggag | 600 |
| aagactttca | gacaacagag | aaaagaacac | ataagggaga | gcatgaagaa | actcttgggt | 660 |
| ccaaagaata | gtgaaggatt | gcattctgca | cgtgatgtgc | ctgtggtagc | catattgggt | 720 |
| tcaggtgggg | gtttccgagc | catggtggga | ttctctggtg | tgatgaaggc | attatacgaa | 780 |

```
tcaggaattc tggattgtgc tacctacgtt gctggtcttt ctggctccac ctggtatatg    840
tcaaccttgt attctcaccc tgattttcca gagaaagggc cagaggagat taatgaagaa    900
ctaatgaaaa atgttagcca caatcccctt ttacttctca caccacagaa agttaaaaga    960
tatgttgagt ctttatggaa gaagaaaagc tctggacaac ctgtcacctt tactgacatc   1020
tttgggatgt taataggaga aacactaatt cataatagaa tgaatactac tctgagcagt   1080
ttgaaggaaa aagttaatac tgcacaatgc cctttacctc ttttcacctg tcttcatgtc   1140
aaacctgacg tttcagagct gatgtttgca gattgggttg aatttagtcc atacgaaatt   1200
ggcatggcta aatatggtac ttttatggct cccgacttat ttggaagcaa atttttttatg   1260 ggaacagtcg ttaagaagta tgaagaaaac cccttgcatt tcttaatggg tgtctggggc   1320
agtgcctttt ccatattgtt caacagagtt ttgggcgttt ctggttcaca aagcagaggc   1380
tccacaatgg aggaagaatt agaaaatatt accacaaagc atattgtgag taatgatagc   1440
tcggacagtg atgatgaatc acacgaaccc aaaggcactg aaaatgaaga tgctggaagt   1500
gactatcaaa gtgataatca agcaagttgg attcatcgta tgataatggc cttggtgagt   1560
gattcagctt tattcaatac cagagaagga cgtgctggga aggtacacaa cttcatgctg   1620
ggcttgaatc tcaatacatc ttatccactg tctcctttga gtgactttgc cacacaggac   1680 tccttttgatg atgatgaact ggatgcagct gtagcagatc ctgatgaatt tgagcgaata   1740
tatgagcctc tggatgtcaa agtaaaaag attcatgtag tggacagtgg gctcacattt   1800
aacctgccgt atcccttgat actgagacct cagagagggg ttgatctcat aatctccttt   1860
gacttttctg caaggccaag tgactctagt cctccgttca aggaacttct acttgcagaa   1920
aagtgggcta aaatgaacaa gctccccttt ccaaagattg atccttatgt gtttgatcgg   1980
gaagggctga aggagtgcta tgtctttaaa cccaagaatc ctgatatgga aaagattgc    2040 ccaaccatca tccactttgt tctgccccaac atcaacttca gaaagtacaa ggctccaggt   2100
gttccaaggg aaactgagga agagaaagaa atcgctgact tgatattttt tgatgacccca   2160 gaatcaccat tttcaacctt caattttcaa tatccaaatc aagcattcaa aagactacat   2220
gatcttatgc acttcaatac tctgaacaac attgatgtga taaagaagc catggttgaa   2280 agcattgaat atagaagaca gaatccatct cgttgctctg ttttcccttag taatgttgag   2340 gcaagagat ttttcaacaa ggagtttcta agtaaaccca agcatagtt catgtactgg    2400 aaatggcagc agtttctgat gctgaggcag tttgcaatcc catgacaact ggatttaaaa   2460
gtacagtaca gatagtcgta ctgatcatga gagactggct gatactcaaa gttgcagtta   2520
cttagctgca tgagaataat actattataa gttaggtgac aaatgatgtt gattatgtaa   2580
ggatatactt agctacattt tcagtcagta tgaacttcct gatacaaatg tagggatata   2640 tactgtatt ttaaacattt ctcaccaact ttcttatgtg tgttcttttt aaaaatttt    2700 tttcttttaa aatatttaac agttcaatct caataagacc tcgcattatg tatgaatgtt   2760
attcactgac tagatttatt cataccatga gacaacacta tttttattta tatatgcata   2820
tatatacata catgaaataa atacatcaat ataaaaataa aaaaaaacgg aattc        2875
```

<210> SEQ ID NO 3
<211> LENGTH: 144
<212> TYPE: PRT
<213> ORGANISM: Homo sapiens

<400> SEQUENCE: 3

```
Met Lys Thr Leu Leu Leu Leu Ala Val Ile Met Ile Phe Gly Leu Leu
1               5                   10                  15
```

Gln Ala His Gly Asn Leu Val Asn Phe His Arg Met Ile Lys Leu Thr
            20                  25                  30

Thr Gly Lys Glu Ala Ala Leu Ser Tyr Gly Phe Tyr Gly Cys His Cys
        35                  40                  45

Gly Val Gly Gly Arg Gly Ser Pro Lys Asp Ala Thr Asp Arg Cys Cys
50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
            85                  90                  95

Cys Ala Lys Gln Asp Ser Cys Arg Ser Gln Leu Cys Glu Cys Asp Lys
        100                 105                 110

Ala Ala Ala Thr Cys Phe Ala Arg Asn Lys Thr Thr Tyr Asn Lys Lys
            115                 120                 125

Tyr Gln Tyr Tyr Ser Asn Lys His Cys Arg Gly Ser Thr Pro Arg Cys
130                 135                 140

<210> SEQ ID NO 4
<211> LENGTH: 749
<212> TYPE: PRT
<213> ORGANISM: Homo sapiens

<400> SEQUENCE: 4

Met Ser Phe Ile Asp Pro Tyr Gln His Ile Ile Val Glu His Gln Tyr
1               5                   10                  15

Ser His Lys Phe Thr Val Val Leu Arg Ala Thr Lys Val Thr Lys
            20                  25                  30

Gly Ala Phe Gly Asp Met Leu Asp Thr Pro Asp Pro Tyr Val Glu Leu
        35                  40                  45

Phe Ile Ser Thr Thr Pro Asp Ser Arg Lys Arg Thr Arg His Phe Asn
        50                  55                  60

Asn Asp Ile Asn Pro Val Trp Asn Glu Thr Phe Glu Phe Ile Leu Asp
65                  70                  75                  80

Pro Asn Gln Glu Asn Val Leu Glu Ile Thr Leu Met Asp Ala Asn Tyr
            85                  90                  95

Val Met Asp Glu Thr Leu Gly Thr Ala Thr Phe Thr Val Ser Ser Met
        100                 105                 110

Lys Val Gly Glu Lys Lys Glu Val Pro Phe Ile Phe Asn Gln Val Thr
            115                 120                 125

Glu Met Val Leu Glu Met Ser Leu Glu Val Cys Ser Cys Pro Asp Leu
130                 135                 140

Arg Phe Ser Met Ala Leu Cys Asp Gln Glu Lys Thr Phe Arg Gln Gln
145                 150                 155                 160

Arg Lys Glu His Ile Arg Glu Ser Met Lys Lys Leu Leu Gly Pro Lys
            165                 170                 175

Asn Ser Glu Gly Leu His Ser Ala Arg Asp Val Pro Val Val Ala Ile
        180                 185                 190

Leu Gly Ser Gly Gly Phe Arg Ala Met Val Gly Phe Ser Gly Val
        195                 200                 205

Met Lys Ala Leu Tyr Glu Ser Gly Ile Leu Asp Cys Ala Thr Tyr Val
210                 215                 220

Ala Gly Leu Ser Gly Ser Thr Trp Tyr Met Ser Thr Leu Tyr Ser His
225                 230                 235                 240

Pro Asp Phe Pro Glu Lys Gly Pro Glu Glu Ile Asn Glu Glu Leu Met
            245                 250                 255

-continued

Lys Asn Val Ser His Asn Pro Leu Leu Leu Thr Pro Gln Lys Val
            260                 265                 270

Lys Arg Tyr Val Glu Ser Leu Trp Lys Lys Ser Ser Gly Gln Pro
            275                 280                 285

Val Thr Phe Thr Asp Ile Phe Gly Met Leu Ile Gly Glu Thr Leu Ile
290                 295                 300

His Asn Arg Met Asn Thr Thr Leu Ser Ser Leu Lys Glu Lys Val Asn
305                 310                 315                 320

Thr Ala Gln Cys Pro Leu Pro Leu Phe Thr Cys Leu His Val Lys Pro
                325                 330                 335

Asp Val Ser Glu Leu Met Phe Ala Asp Trp Val Glu Phe Ser Pro Tyr
            340                 345                 350

Glu Ile Gly Met Ala Lys Tyr Gly Thr Phe Met Ala Pro Asp Leu Phe
            355                 360                 365

Gly Ser Lys Phe Phe Met Gly Thr Val Val Lys Lys Tyr Glu Glu Asn
370                 375                 380

Pro Leu His Phe Leu Met Gly Val Trp Gly Ser Ala Phe Ser Ile Leu
385                 390                 395                 400

Phe Asn Arg Val Leu Gly Val Ser Gly Ser Gln Ser Arg Gly Ser Thr
                405                 410                 415

Met Glu Glu Glu Leu Glu Asn Ile Thr Thr Lys His Ile Val Ser Asn
            420                 425                 430

Asp Ser Ser Asp Ser Asp Glu Ser His Glu Pro Lys Gly Thr Glu
            435                 440                 445

Asn Glu Asp Ala Gly Ser Asp Tyr Gln Ser Asp Asn Gln Ala Ser Trp
450                 455                 460

Ile His Arg Met Ile Met Ala Leu Val Ser Asp Ser Ala Leu Phe Asn
465                 470                 475                 480

Thr Arg Glu Gly Arg Ala Gly Lys Val His Asn Phe Met Leu Gly Leu
                485                 490                 495

Asn Leu Asn Thr Ser Tyr Pro Leu Ser Pro Leu Ser Asp Phe Ala Thr
            500                 505                 510

Gln Asp Ser Phe Asp Asp Asp Glu Leu Asp Ala Ala Val Ala Asp Pro
            515                 520                 525

Asp Glu Phe Glu Arg Ile Tyr Glu Pro Leu Asp Val Lys Ser Lys Lys
530                 535                 540

Ile His Val Val Asp Ser Gly Leu Thr Phe Asn Leu Pro Tyr Pro Leu
545                 550                 555                 560

Ile Leu Arg Pro Gln Arg Gly Val Asp Leu Ile Ser Phe Asp Phe
                565                 570                 575

Ser Ala Arg Pro Ser Asp Ser Ser Pro Phe Lys Glu Leu Leu Leu
            580                 585                 590

Ala Glu Lys Trp Ala Lys Met Asn Lys Leu Pro Phe Pro Lys Ile Asp
            595                 600                 605

Pro Tyr Val Phe Asp Arg Glu Gly Leu Lys Glu Cys Tyr Val Phe Lys
610                 615                 620

Pro Lys Asn Pro Asp Met Glu Lys Asp Cys Pro Thr Ile Ile His Phe
625                 630                 635                 640

Val Leu Ala Asn Ile Asn Phe Arg Lys Tyr Lys Ala Pro Gly Val Pro
                645                 650                 655

Arg Glu Thr Glu Glu Glu Lys Glu Ile Ala Asp Phe Asp Ile Phe Asp
            660                 665                 670

Asp Pro Glu Ser Pro Phe Ser Thr Phe Asn Phe Gln Tyr Pro Asn Gln

```
                    675                 680                 685

Ala Phe Lys Arg Leu His Asp Leu Met His Phe Asn Thr Leu Asn Asn
        690                 695                 700

Ile Asp Val Ile Lys Glu Ala Met Val Glu Ser Ile Glu Tyr Arg Arg
705                 710                 715                 720

Gln Asn Pro Ser Arg Cys Ser Val Ser Leu Ser Asn Val Glu Ala Arg
                725                 730                 735

Arg Phe Phe Asn Lys Glu Phe Leu Ser Lys Pro Lys Ala
            740                 745

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Leu Ser Tyr Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Leu Ser Tyr Arg
1               5

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttgtcaccc aagaactctt ac                                            22

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggagggagg gtatgaga                                                 18

<210> SEQ ID NO 9
<211> LENGTH: 18
<212> TYPE: DNA
<213> ORGANISM: Homo sapiens

<400> SEQUENCE: 9
gaggtaaatg gtattctc                                                 18
```